US008371290B2

(12) United States Patent
Haveri

(10) Patent No.: US 8,371,290 B2

(45) Date of Patent: Feb. 12, 2013

(54) DEVICE FOR DELIVERY AND REGULATION OF VOLATILE FLUIDS INTO INSPIRATORY GAS

(75) Inventor: Heikki Antti Mikael Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 1141 days.

(21) Appl. No.: 12/248,067

(22) Filed: Oct. 9, 2008

(65) Prior Publication Data

US 2009/0095288 A1 Apr. 16, 2009

(30) Foreign Application Priority Data

Oct. 16, 2007 (EP) .................................... 07396006

(51) Int. Cl.
*A61M 11/00* (2006.01)

(52) U.S. Cl. .......... 128/200.16; 128/200.14; 128/203.12

(58) Field of Classification Search ............. 128/200.16, 128/200.18, 200.14, 203.12; 239/102.2, 239/338, 68
See application file for complete search history.

(56) References Cited

U.S. PATENT DOCUMENTS

| | | | | |
|---|---|---|---|---|
| 3,790,079 | A * | 2/1974 | Berglund et al. | 239/3 |
| 3,812,854 | A | 5/1974 | Michaels et al. | |
| 4,533,082 | A | 8/1985 | Maehara et al. | |
| 6,530,370 | B1 * | 3/2003 | Heinonen | 128/200.16 |
| 7,104,463 | B2 * | 9/2006 | Litherland et al. | 239/4 |
| 2003/0140919 | A1 | 7/2003 | Heinonen | |
| 2003/0196660 | A1 | 10/2003 | Haveri | |
| 2005/0230495 | A1 | 10/2005 | Feriani et al. | |

* cited by examiner

*Primary Examiner* — Steven Douglas

(74) *Attorney, Agent, or Firm* — Global Patent Operation

(57) ABSTRACT

An apparatus for discharging fluid for a subject breathing. The apparatus includes a fluid cavity for conveying a fluid to be discharged; a valve for guiding the flow of fluid through the fluid cavity; a control unit for controlling the valve for guiding the flow of fluid; a first housing having a wall and a hole on this wall for fluid flowing through the fluid cavity; a first member apart from the first housing having holes discharging fluid through them for the subject breathing; a chamber between the first member and the first housing for receiving the fluid coming along the fluid cavity; a vibrator making the first member to vibrate and discharge fluid through the holes to a subject breathing tube. The vibrator is in contact with the first member through a transmitter extending towards the chamber and which transmitter transmits the vibration effect from the vibrator to the first member.

17 Claims, 3 Drawing Sheets

DEVICE FOR DELIVERY AND REGULATION OF VOLATILE FLUIDS INTO INSPIRATORY GAS

CROSS-REFERENCE TO RELATED APPLICATIONS

This application claims priority under 35 U.S.C. §119(a)-(d) to prior-filed, co-pending European patent application serial number 07396006.4, filed on 16 Oct. 2007, which is hereby incorporated by reference in its entirety.

FIELD OF THE INVENTION

This disclosure relates to a delivery device for discharging fluid into small droplets that is fed into an inspiratory gas flow of a subject making the delivery and regulation of fluid effective.

BACKGROUND OF THE INVENTION

While anestetizing patients anesthetic agent is typically held in a vessel having a liquid space and a gas space in which vessel the agent is vaporized into a carrying gas, which may require heating depending on physical features of the agent. Vaporized anesthetic agent mixed with the carrying gas is then led to a patient for inspiration. However, vaporizers like these are producing vapor continuously and not at times when the vapor is useful to feed to a patient. Also it takes a lot of room which is limited in operating rooms where these devices are used.

Another type of vaporizer is also known where anesthetic agent is supplied from a liquid reservoir to a piezoelectric pump which is capable of generating liquid droplets into an inspiration of a patient. However, this kind of pump causes difficulties while cleaning it after any use. Especially there is a heating element in an airway leading to a patient which is very difficult to clean. Some cleaning devices may even break the device. The whole unit should be sterilized before using it with another patient. Anesthetic agents may dissolve glue joints needed in this structure to fix piezoelectric element to other structure surrounding. Anesthetic agents further have very low surface tension which means that it does not behave like many common nebulized agents and thus it is expected anesthetic agents may cause problems with this kind of products.

Further various technologies used with nebulizers to deliver atomized medicine to a patient are known. For instance it is well-known to use a thin mesh plate having holes and which plate is vibrated at ultrasonic frequencies to cause a liquid to pass through the holes to atomize the liquid. Vibration may be produced by measuring current, voltage or phase angle taken by the element or by measuring the resistance of the strain gauge attached to vibrator. As the vibrating element there is typically used a piezoelectric element adjacent an upper surface of the mesh plate to vibrate this plate. The piezoelectric element is spaced from the mesh plate by a small gap and secured to it about its periphery e.g. by conductive glue, brazing, welding which may be damaged by anesthetic agents. There is a sensor to measure liquid supplied to the surface of the mesh plate and this is automatically controlled to maintain a desired volume of liquid on the surface of a mesh plate. Or alternatively there are two plates spaced from each other so that a volume is defined between them and these plates are formed to establish a mutual capacitance reflecting the amount of liquid in the volume. The measured capacitance reflects the amount of liquid in the nebulizer which information can be used to control the supply of liquid into the volume and through the holes of one of the plates. Again cleaning is a problem when the unit is reused with another patient especially because it is one compact unit. Also in this case especially anesthetic agents dissolve glue joints of the structure. Further measurement of electrical conductivity of anesthetic agents cannot be exploited in this nebulizer, because anesthetic agents are insulants. Anesthetic agents have very low surface tension which means that it does not behave like many common nebulized agents and thus it is expected anesthetic agents may cause problems with this kind of products.

There are also nebulizers having a structure where a vibrator is arranged opposite to holes of a detachable mesh member pushing a liquid directly through the holes. A longitudinal movement of the vibrator away from the mesh member causes a suction effect to a reservoir whereupon the liquid starts to flow to a volume between the holes of the mesh member and the vibrator and when the vibrator is moving towards the member the liquid is pushed through the holes forming small droplets for a patient breathing. Thus atomization of liquid is not achieved by a vibration of the membrane but the oscillator itself is pushing the liquid. Especially this does not work with anesthetic agents if there is no active dosing system for the liquid. The surface tension of anesthetic agents is so low that agents flow from the reservoir to the member and are able to escape through those holes, too. Also a production of droplets ceases if the member's output surface is getting wet, which happens from time to time.

BRIEF DESCRIPTION OF THE INVENTION

The above-mentioned shortcomings, disadvantages and problems are addressed herein which will be understood by reading and understanding the following specification.

In an embodiment, an apparatus for discharging fluid for a subject breathing includes a fluid conveying means for conveying a fluid to be discharged and a means for guiding the flow of fluid through the fluid conveying means and a control means for controlling the means for guiding the flow of fluid. The apparatus for discharging fluid for a subject breathing also includes a first housing having a wall and hole on said wall for fluid flowing through the fluid conveying means and a first member apart from the first housing having holes discharging fluid through them for the subject breathing. The apparatus for discharging fluid for a subject breathing also includes a chamber between the first member and the first housing for receiving the fluid coming along the fluid conveying means and a vibrator making the first member to vibrate and discharge fluid through the holes of the first member to a breathing circuit. The vibrator is in contact with the first member through a transmission means extending towards the chamber and which transmission means transmits the vibration effect from the vibrator to the first member.

In another embodiment, an apparatus for discharging fluid for a subject breathing includes a fluid cavity for conveying a fluid to be discharged and a valve for guiding the flow of fluid through the fluid cavity and a control unit for controlling the valve for guiding the flow of fluid. The apparatus for discharging fluid for a subject breathing also includes a first housing having a wall and a hole for fluid flowing through said fluid cavity and a first member apart from the first housing having holes discharging fluid through them for the subject breathing. The apparatus for discharging fluid for a subject breathing also includes a chamber between the first member and the first housing for receiving the fluid coming along said fluid cavity and a vibrator making said first member to vibrate and discharge fluid through the holes of the first member to a breathing circuit. The vibrator is in contact with the first member through a transmitter extending towards the chamber and which transmitter transmits the vibration effect from the vibrator to the first member.

Various other features, objects, and advantages of the invention will be made apparent to those skilled in art from the accompanying drawings and detailed description thereof.

DETAILED DESCRIPTION OF THE INVENTION

Figure 1:
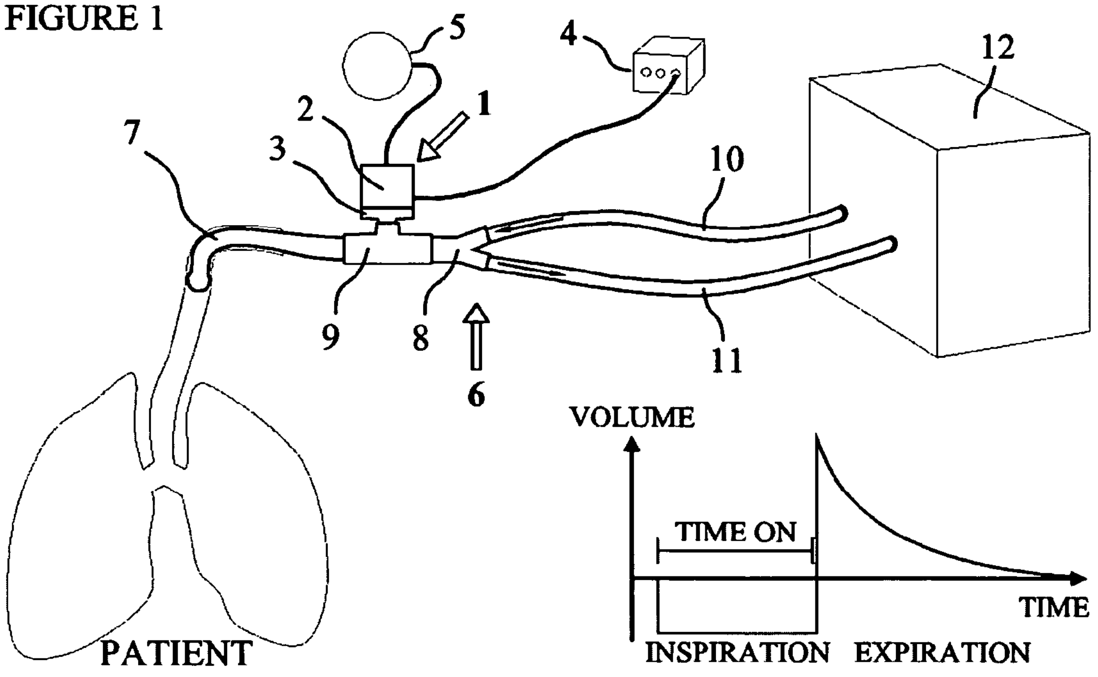
FIG. 1 shows a general view of an apparatus of an embodiment of the invention in an operating environment.

FIG. 1 shows a schematic view of fluid delivery device and peripheral devices it can be connected to. The delivery device transforms liquid into small droplets or "spray" that is immediately vaporized into the inspiratory gas flow making the delivery and regulation of a liquid efficient. Especially, if the liquid is a volatile anesthetic, delivery and regulation is more efficient compared to conventional vaporizers. The delivery device can be used as nebulizer or atomizer as well. The device is inexpensive, energy-efficient and small in size, which enables its connection close to the patient. Dead space between the patient and the device is very small and the concentration of anesthetics in the inspiratory gas entering the patient can be raised high quickly, which makes the response time to concentration changes short.

The delivery device 1 comprises a device body 2 and patient connector 3, which connect together. Control means 4, such as control unit, containing electronics, software and electrical power source to control the device, may be located further, but preferably it is integrated inside the delivery device. Liquid form anesthetic agent or liquid form other substance e.g. medicine or moisturizing agent is stored into fluid reservoir 5, which can be located further away or close to or within the fluid delivery device, from where the fluid is delivered in to the delivery device. The delivery device is further connected to breathing circuit 6 preferably between intubation tube 7 and a first connector 8 such as Y-piece having three branches through a second connector 9 having three ports. Two other branches of Y-piece are connected to an inspiratory gas tube 10 and an expiratory gas tube 11. The delivery device is connected to the third port aside of second connector 9 so that the breathing gas flows preferably straight through the two adjacent ports of second connector 9, that are in connection to the breathing circuit. Other end of intubation tube 7 is connected to the patient.

Figure 2:
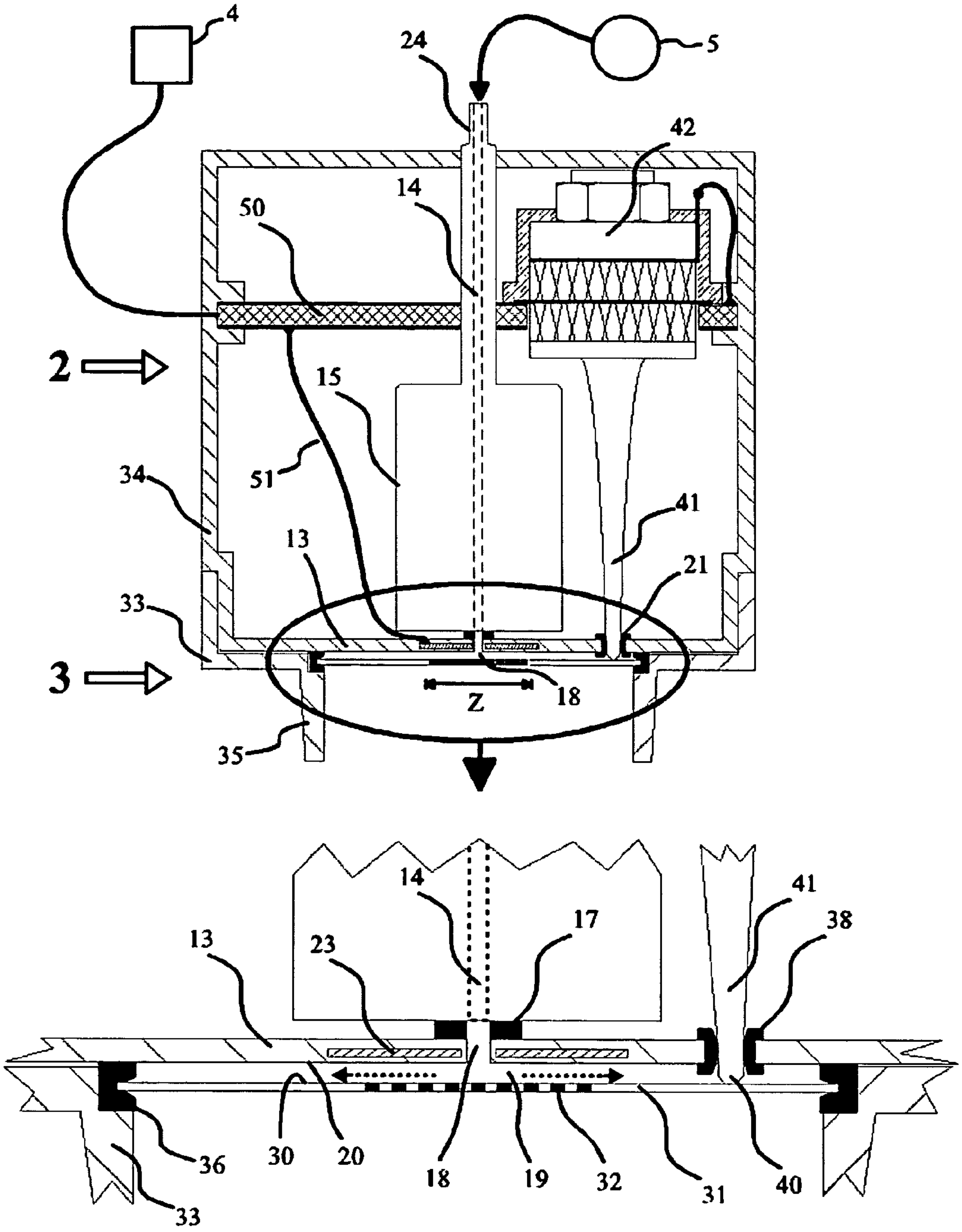
FIG. 2 shows a schematic view of a delivery device of the embodiment of the invention.

Volatile anesthetic fluids are very difficult to handle as they are powerful solvents, their surface tension is very small and they tend to pass through even the smallest openings. Therefore parts that are in straight contact with the anesthetic should be made of materials such as anesthetic endurable metal, but preferably anesthetic endurable plastic or similar to make the device less expensive. FIG. 2 shows a schematic view of delivery device and beneath the schematic view is a more detailed, enlarged view of the functional part that breaks up the liquid into small droplets or spray. The device body 2 which comprises a first housing 34 is reusable and thus non-disposable and therefore all the technically complicated, more expensive components are placed inside it. The patient connector 3 is designed detachable and disposable and therefore it has to be very simple and low-cost, but of course it can be cleanable and reusable as well. The benefit of disposability is due to fact that patient connector separates the patient side from the device side preventing bacteria and viruses to enter the reusable parts. This reduces the cleaning work done by hospital personnel and improves the patient safety.

Patient connector 3 comprises a second housing 33 preferably made of anesthetic endurable plastic or similar. The second housing 33 has a bayonet type of connection on the surfaces of housing 33 towards first housing 34, having a wall 13 with a hole 18 for fluid, or similar to connect patient connector 3 to the first housing of device body 2 and a third connector 35 which may be of luer fitting type or similar to connect the patient connector 3 to the second connector 9 in connection to breathing circuit. It is also possible to combine the second housing 33 and second connector 9 to form only one part. A first member 31 is fitted and sealed in to the second housing 33 through a second sealing 36, which is advantageously made of anesthetic endurable elastic material, to prevent liquid anesthetic to traverse or leak to the patient side of the patient connector 3, but it is also used to separate the patient side of the breathing circuit from the side of delivery device to prevent contamination between different patients.

The first member 31 such as a plate has a group of holes 32, for example machined with laser, chemically etched or similar, in to the area in the middle of first member 31. The diameter of straight holes is preferably between 100 nm-500 μm and the height of holes 32 becomes from the thickness of first member 31, which is preferably between 10-500 μm. First member 31 can be made of any material suitable for establishing vibrations at ultrasonic frequencies and to have a group of holes 32, but preferably it is made of electrically conductive metal such as stainless steel, brass or similar. First member 31 can also be implemented by gluing, soldering or similarly attaching a smaller diaphragm, made of metal, ceramic or similar material, having holes 32 in to an opening in a larger first member made of metal or similar that function as a rigid frame or a body for the diaphragm to compose first member 31.

When patient connector 3 is connected to device body 2 second sealing 36 in patient connector 3 tightens against the lower surface 20 of device body 2 forming a chamber 19, which is advantageously sealed, between the lower surface 20 of device body 2 and upper surface 30 of first member 31.

First member 31 settles close to the lower surface 20 of device body 2 so that the upper surface 30 of first member 31 touches a tip 40 of transmission means 41 of a vibrator 42, which perforates the wall 13 of the first housing 34 and goes through third sealing 38, which may be made of an anesthetic endurable elastic material, which is used to prevent anesthetic to flow inside the device body 2 and thus the first housing 34. Instead of an aperture 21 on the wall 13 there may be a wall or a part of wall made of flexible material bending towards the vibrating first member whereby the transmission means 41 such as transmitter, which extends towards the chamber 19, is able to vibrate the first member without piercing the wall 13.

The dielectric of volatile anesthetics is high and the capacitance they produce between the capacitive electrodes is also high and thus the amount of liquid can be easily measured by measuring a capacitance between an electrically conductive element 23 such as a conductive plate, inside the lower surface 20 of the wall 13 of the first housing 34 made of plastic or similar and the electrically conductive vibrating first member 31 in patient connector 3. Element 23 and first member 31 thus function as electrodes for capacitor and the space between element 23 and first member 31 in chamber 19 function as a dielectric, which value alters between the dielectric of air which is the case there is no anesthetic in chamber 19 and the maximum dielectric as the space between element 23 and first member 31 in chamber 19 is filled up with the anesthetic. The capacitive measurement becomes more sensitive as the distance between element 23 and first member 31 is decreased whereas the amount of anesthetic on the plate is also decreased. A suitable distance between element 23 and first member 31 is between 0.2 mm to 2 mm. Volatile anesthetics are good electrical insulators and thus their electrical conductivity is small so it is also possible to have electrically fully conductive lower surface 20 of device body 2 to enable for example capacitive measurement.

The electrical connection 51 to element 23 can be established from the electronics board 50 in the case the device body 2 is made of plastic, whereas the electrical connection to vibrating first member 31 can be implemented through the tip 40 of transmission means 41 of vibrator 42 that also connects to electrical ground of control means 4. The vibrator 42 is preferably a piezoelectric vibrator or similar, which is controlled by the control means 4. The vibrating motion generated by the transducer is normally too low for practical use and so it is necessary to magnify or amplify the vibrating motion. This function can be implemented with a horn shaped ultrasonic vibrator-transmission means 42, 41 shown in FIG. 2. Vibrator has a construction of thin piezoelectric elements preferably shape of the rings, normally two or four, that are clamped between a pair of acoustically low loss metal end masses, preferably made of aluminum or titanium, composing a resonant element functioning in the compression mode. The assembly would be designed so that the overall length is one half-wave at the required frequency of operation, although they can be designed in multiples of half wavelengths also. Two piezoelectric elements are positioned near to the point of maximum stress in a half-wave resonant assembly. Because the elements are pre-polarized they can be so arranged that they are mechanically aiding but electrically opposing. This feature enables both end masses to be at a mechanical earth potential, which is in practice also the connection point of vibrator to electronics board 50 and through that to device body 2. The assembly is clamped together by means of a high tensile bolt, which ensures the ceramics are in compression at maximum vibrator displacement. Vibrators constructed in this way can have potential efficiencies of 98% and will handle power transfers of hundreds of watts when employed in a mode of continuous operation. The maximum peak to peak displacements at the vibrator radiating face would be around 100-200 microns when operating at a frequency of 1-500 kHz.

Liquid form anesthetic agent is delivered from the fluid reservoir 5 to the delivery device 1 through an inlet 24 and a fluid conveying means 14 of means 15 for guiding the flow of fluid. Means 15 for guiding the flow of fluid is preferably positioned inside the first housing 34 of the device body 2, but can be located between the inlet 24 and reservoir 5 as well. Means 15 for guiding the flow of fluid can be controlled by the electrical signal from control means 4, to apportion anesthetic along the fluid conveying means 14 through a first sealing 17 and hole 18 opening in to the chamber 19. The control of means 15 for guiding the flow of fluid is for instance based on the presence or the amount of liquid anesthetic in the space between the two element 23 and first member 31, which is known in the art. The value of capacitance proportional to the amount of liquid in chamber 19 is transmitted to control means 4 as an electrical signal, which is then used for controlling the means 15 for guiding the flow of fluid. Thus if there is no or a little amount of anesthetic fluid between the capacitive electrodes, control means 4 gets electrical signal of low capacitance and the means 15 for guiding the flow of fluid is opened to allow the flow of anesthetic fluid into the chamber 19 as long as the diameter of fluid column between element 23 and first member 31 exceeds the edges of element 23, which means that the capacitance reaches its maximum value and all the holes 32 are wetted. Then the control means gets electrical signal proportional to maximum capacitance and means 15 for guiding the flow of fluid is closed again to stop the flow of fluid until the fluid column between element 23 and first member 31 degreases below the edges of element 23 due to spraying of fluid and is opened again.

Figure 3:
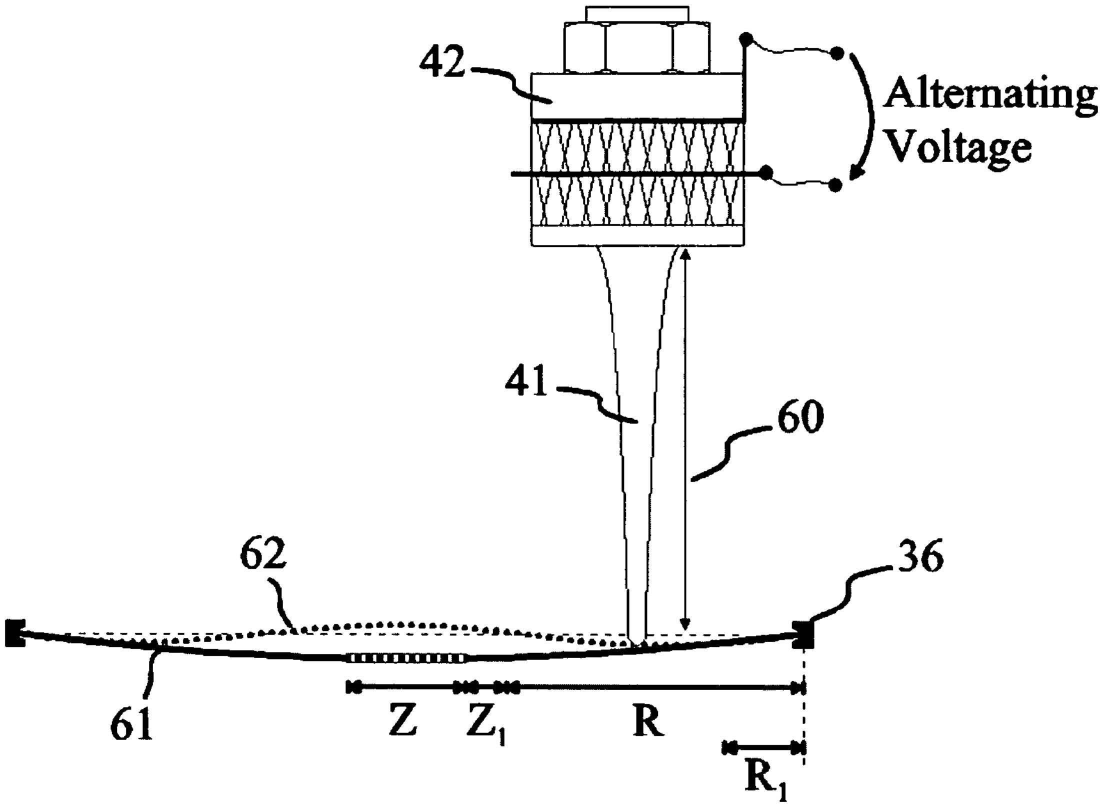
FIG. 3 is a schematic view showing an operation of the delivery device of FIG. 2.

To generate spray or anesthetic vapor an alternating electrical signal is connected to vibrator 42. Electrical energy is converted to longitudinal mechanical movement of the transmission means that is transferred via tip 40 of transmission means 41 towards vibrating first member 31, positioned transversely against the transmission means, which is then forced to vibrate in the bending mode. Fluid apportioned by the means 15 for guiding the flow of fluid on the vibrating first member 31 is squeezed through the holes in the middle of the first member as little droplets as a result of back and forth movement of first member 31, which droplets then evaporate into the inspiratory breathing gas flowing in the breathing circuit. The longitudinal movement of vibrator 42 can be magnified depending on the contact point of tip 40 and vibrating first member 31 along the radius of first member 31. The magnification increases proportional to the distance of contact point measured from the center, along the radius, towards the circumference of first member 31. Of course the magnification also depend on the applied frequency of mechanical vibration of vibrator 42, as well as the mechanical stiffness of first member 31. The amplitude of vibration may be smaller when the fundamental frequency of longitudinal vibration 60 of vibrator 42 is too high in regard to the mechanical stiffness of first member 31, as shown in a simplified schematic view in FIG. 3. Mechanically too soft first member 31 starts to vibrate at the frequency of one of the sub-harmonics 62 of fundamental frequency of vibrator 42 and its amplitude of vibration may be smaller compared to the amplitude of vibration 61 of rigid enough first member vibrating at fundamental frequency.

The tip 40 of the transmission means 41 has a contacting point on said vibrating first member advantageously only in an area R and outside an area Z of holes 32 which is between an outer edge of vibrating first member and the area Z. Thus area Z covers besides holes 32 but also the area between these holes. Furthermore it may be advantageous and even necessary to extend the area Z towards the outer edge of vibrating first member by the distance $Z_1$ by leaving more space around the holes in the area Z to increase the durability of holes since the vibrating tip 40 may fracture isthmuses between the holes easily if the tip 40 is placed too close to the area Z of holes. It is also beneficial to leave distance $R_1$ between the tip 40 and outer edge of vibrating first member although the amplification of bowing of vibrating first member increases rapidly as the tip 40 is moved closer to the outer edge of vibrating first member. If the distance $R_1$ is too small the transmission means 41 has to do more work against elastic second sealing 36 to bow the vibrating first member, which decreases the efficiency to produce vibrations, furthermore as the vibrating first member starts to bows due to the increase in length of transmission means 41 within one cycle of longitudinal vibration the tip 40 may slip and bend towards the center of vibrating first member braking the transmission means or deteriorating its functioning. The advisable distance for $Z_1$ from the edge of area Z towards the edge of vibrating first member is approximately 0.5-2 mm, whereas the advisable distance for $R_1$ from the edge towards the center of vibrating first member is approximately ⅙ of the radius of the first member. Further a contacting point might be only on an sector of said vibrating first member which is less than 360 degrees around its periphery. It may well be only on the sector of the vibrating first member which is less than 180 degrees around its periphery. It is quite possible to arrange the contacting point only on the sector which is less than 90 degrees around the periphery of the first member, which is the case shown in FIGS. 2 and 3.

The amount of evaporated anesthetic can be regulated by adjusting the spray time and since it is optimal to spray anesthetic in to the inspiratory gas to improve delivery efficiency, which is the actual volume of anesthetic agent delivered in to the patient, it is useful to adjust spray time between the start and the end of inspiration. Alternatively the spray efficiency can be adjusted. The production rate of vaporized agent is independent of the fresh gas flow, which reduces the consumption of volatile anesthetics during anesthesia. The delivery of anesthetic agent can be advantageously synchronized to the start of inspiration and expiration by detecting both as explained in the patent U.S. Pat. No. 6,978,779. The delivery can as well be synchronized to spirometric measurement of a patient by supplying an electrical signal from patient spirometry to control means 4, which is comparable to inspiration and expiration or the synchronization can be executed through electrical signal from ventilator as well, which informs the control means 4 of the beginning of inspiration and expiration. To ensure that the anesthetic agent does not seep through the holes in the first member 31 while the spraying is turned of during expiration it is useful to close the means 15 for guiding the flow of fluid and to disable the capacitive measurement by the control means 4 thus preventing fluid to flow in to the chamber 19 despite of the signal state of capacitive measurement. As inspiration starts again the capacitive measurement is enabled and control means 4 allows the means 15 for guiding the flow of fluid to be turned on again to feed the fluid in to the chamber 19 to keep the surface of first member 31 wetted.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. An apparatus for delivering anesthetic to a breathing circuit, the apparatus comprising:
- a fluid conveyor;
- a guiding member configured to guide a flow of fluid through said fluid conveyor;
- a control unit configured to control said guiding member;
- a first housing comprising a wall, the wall defining a hole therethrough configured to allow passage of fluid from an outlet of said fluid conveyor;
- a first member spaced apart from said first housing, the first member defining a plurality of openings for discharging fluid through the first member;
- a chamber defined between said first member and said wall of said first housing configured to receive fluid from said fluid conveyor;
- a vibrator configured to vibrate said first member to discharge fluid through said openings in said first member and towards a breathing circuit and a transmission member configured to transmit vibratory motion from said vibrator to said first member; wherein said wall of said first housing defines an aperture and a portion of said transmission member extends through said aperture and abuts said first member.

2. The apparatus of claim 1, wherein said vibrator is disposed inside said first housing.

3. The apparatus of claim 1, further comprising a seal disposed in said aperture.

4. The apparatus of claim 1, wherein a tip of said transmission member is directly in contact with said first member.

5. The apparatus of claim 4, wherein said tip of said transmission member contacts said first member outside an area of said first member defining said plurality of openings.

6. The apparatus of claim 5, wherein said transmission member has a contacting point on said first member between an outer edge of said first member and said area of said first member defining said plurality of openings.

7. The apparatus of claim 6, wherein said transmission means has a contacting, point only on a sector of said first member which is less than 360 degrees around its periphery.

8. The apparatus of claim 7, wherein said transmission member has a contacting point only on a sector of said first member which is less than 180 degrees around its periphery.

9. The apparatus of claim 8, wherein said transmission member has a contacting point only on an area of said first member which is less than 90 degrees around its periphery.

10. The apparatus of claim 2, wherein said guiding member is disposed in said first housing.

11. The apparatus of claim 2, further comprising an electrically conductive element coupled to said wall of said first housing opposite said first member, said conductive element and said first member forming capacitive electrodes for use in determining an amount of fluid in said chamber.

12. The apparatus of claim 11, wherein the control unit is configured to control said guiding member based in part on an amount of fluid in the chamber.

13. The apparatus of claim 1, further comprising a second housing that is separate and detachable from said first housing, said first member being disposed in said second housing.

14. The apparatus of claim 13, wherein said second housing is located between said first housing and the breathing circuit.

15. The apparatus of claim 1, wherein said vibrator comprises a piezoelectric element.

16. The apparatus of claim 1, further comprising a fluid reservoir configured to hold an anesthetic agent to be discharged.

17. An apparatus for delivering anesthetic to a patient, comprising:
- a fluid conveyor configured to convey a fluid to be delivered to a breathing circuit;
- a valve for guiding the flow of fluid through said fluid conveyor;
- a control unit for controlling said valve;
- a first housing comprising a wall defining a hole configured to allow passage of fluid from an outlet of said fluid conveyor;
- a first member spaced apart from said first housing and defining a plurality of openings configured to discharge fluid through the first member;
- a chamber defined between said first member and said wall of said first housing, the chamber configured to receive fluid from said fluid conveyor;
- a vibrator configured to vibrate said first member to discharge fluid from said chamber through said openings in said first member to the breathing circuit; and
- a transmission member configured to transmit vibratory motion from said vibrator to said first member,
- wherein said wall of said first housing defines an aperture and a portion of said transmission member extends through said aperture and abuts said first member.

* * * * *

UNITED STATES PATENT AND TRADEMARK OFFICE

CERTIFICATE OF CORRECTION

PATENT NO. : 8,371,290 B2
APPLICATION NO. : 12/248067
DATED : February 12, 2013
INVENTOR(S) : Haveri It is certified that error appears in the above-identified patent and that said Letters Patent is hereby corrected as shown below:

In the Claims:

In Column 7, Lines 59-65, in Claim 1, delete "openings in said first member and towards a breathing circuit and a transmission member configured to transmit vibratory motion from said vibrator to said first member; wherein said wall of said first housing defines an aperture and a portion of said transmission member extends through said aperture and abuts said first member." and
insert -- openings in said first member and towards a breathing circuit; and
a transmission member configured to transmit vibratory motion from said vibrator to said first member;
wherein said wall of said first housing defines an aperture and a portion of said transmission member extends through said aperture and abuts said first
member. --, therefor.

In Column 8, Line 14, in Claim 7, delete "means" and insert -- member --, therefor.

In Column 8, Line 14, in Claim 7, delete "contacting," and insert -- contacting --, therefor.

In Column 8, Line 40, in Claim 16, delete "anesthetic agent" and
insert -- anesthetic or anesthetic agent --, therefor.

Signed and Sealed this
Fourteenth Day of May, 2013

Teresa Stanek Rea
*Acting Director of the United States Patent and Trademark Office*